(12) United States Patent
Hsu et al.

(10) Patent No.: US 9,694,051 B2
(45) Date of Patent: Jul. 4, 2017

(54) LONG-ACTING PEPTIDE ANALOGS

(75) Inventors: Sheau Yu Hsu, Menlo Park, CA (US); Chia Lin Chang, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 101 days.

(21) Appl. No.: 14/110,098

(22) PCT Filed: Apr. 5, 2012

(86) PCT No.: PCT/US2012/032333
§ 371 (c)(1),
(2), (4) Date: Dec. 30, 2013

(87) PCT Pub. No.: WO2012/138867
PCT Pub. Date: Oct. 11, 2012

(65) Prior Publication Data
US 2014/0155329 A1 Jun. 5, 2014

Related U.S. Application Data

(60) Provisional application No. 61/473,054, filed on Apr. 7, 2011, provisional application No. 61/474,177, filed on Apr. 11, 2011, provisional application No. 61/474,182, filed on Apr. 11, 2011.

(51) Int. Cl.
| C07K 14/575 | (2006.01) |
| A61K 38/22 | (2006.01) |
| C07K 16/28 | (2006.01) |
| A61K 47/48 | (2006.01) |

(52) U.S. Cl.
CPC ........... *A61K 38/22* (2013.01); *C07K 14/575* (2013.01); *A61K 47/48* (2013.01); *C07K 16/28* (2013.01)

(58) Field of Classification Search
CPC .............. A61K 38/00; A61K 47/48246; A61K 47/48046; C07K 14/47; C07K 14/001; C07K 14/4705; C07K 14/575
See application file for complete search history.

(56) References Cited

U.S. PATENT DOCUMENTS

| 6,239,107 B1 | 5/2001 | Gozes et al. | |
| 6,268,474 B1 | 7/2001 | Smith et al. | |
| 2008/0026995 A1* | 1/2008 | Tosi | A61K 39/0005 435/7.23 |
| 2008/0113411 A1* | 5/2008 | Sheffer | C07K 14/765 435/69.6 |
| 2008/0207501 A1 | 8/2008 | Erickson et al. | |
| 2008/0274952 A1 | 11/2008 | Soares et al. | |
| 2009/0036364 A1 | 2/2009 | Levy et al. | |
| 2009/0088387 A1 | 4/2009 | Castillo et al. | |
| 2009/0175821 A1 | 7/2009 | Bridon et al. | |
| 2009/0186817 A1 | 7/2009 | Ghosh et al. | |
| 2010/0048871 A1 | 2/2010 | Cho et al. | |

FOREIGN PATENT DOCUMENTS

| CN | 101035806 A | 9/2007 | |
| CN | 101208099 A | 6/2008 | |
| DE | WO 2008/022716 A2 * | 2/2008 | ........... C07K 14/575 |
| JP | 1999-502204 A | 2/1999 | |
| JP | 2002-540216 A | 11/2002 | |
| JP | 2008-507280 A | 3/2008 | |
| JP | 2008-515443 A | 5/2008 | |
| NL | WO2006082184 A2 * | 8/2006 | ............. A61K 47/48 |
| WO | WO2012138867 A2 | 10/2012 | |

OTHER PUBLICATIONS

Gault et al. Enhanced cAMP generation and insulin-releasing potency of two novel Tyr1-modified enzyme-resistant forms of glucose-dependent insulinotropic polypeptide is associated with significant antihyperglycaemic activity in spontaneous obesity-diabetes. Biochem J. Nov. 1, 2002 ;367(Pt 3):913-20.*
Methods in Molecular Bology. vol. 35 Peptide Synthesis Protocols Ch 8, Site-Specific Chemical Modification Procedures. pp. 171-185. Edited by M W Pennington and B M Dunn Copynght 1994 Humana Press Inc , Totowa, NJ.*
Dasgupta et al. Lipophilization of somatostatin analog RC-160 with long chain fatty acid improves its antiproliferative and antiangiogenic activity in vitro. Br J Pharmacol. Jan. 2000;129(1):101-9.*
Kostel et al. Purification of a lipid peptide: Method development for Hydrophobic Peptides. Conference abstract presented at ABRF / 1998.*
Santiago et al. Comparison of responses to adrenomedullin and adrenomedullin analogs in the mesenteric vascular bed of the cat. Eur J Pharmacol. Jan. 5, 1995;272(1):115-8.*
Maletinska et al. Angiotensin Analogues Palmitoylated in Positions 1 and 4. J. Med. Chem. 1997, 40, 3271-3279.*
Chapter et al., "Chemical modification of Class II G-protein coupled receptor ligands: Frontiers in the development of peptide analogs as neuroendocrine pharmacological therapies", Pharmacol Ther (2010), 125(1):39.
Jagadish et al., "Squalene-derived Flexible Linkers for Bioactive Peptides", Bioorg Med Chem Lett (2007), 17 (12):3310-3313.
Kato et al., "Adrenonnedullin: A Protective Factor for Blood Vessels", Arterioscler Thromb Vasc Biol. (2005), 25:2480-2487.
Kurtzhals, "How to achieve a predictable basal insulin?", Diabetes Metab (2005), 31(4 Pt 2):4S25-4S33.
Takahashi et al., "Adrenomedullin 2/intermedin in the hypothalamo-pituitary-adrenal axis", J Mol Neurosci (2011), 43 (2):182-192.
Kubo; et al., "Biological properties of adrenomedullin conjugated with polyethylene glycol", Peptides (May 2014), 57:118-121.
Meeran; et al., "Circulating Adrenomedullin Does Not Regulate Systemic Blood Pressure but Increases Plasma Prolactin after Intravenous Infusion in Humans: A Pharmacokinetic Study*", Journal of Clinical Endocrinology and Metabolism (Jan. 1997), 82(1):95-100.

(Continued)

*Primary Examiner* — Satyanarayana R Gudibande
*Assistant Examiner* — Jia-Hai Lee
(74) *Attorney, Agent, or Firm* — Pamela J. Sherwood; Bozicevic, Field & Francis LLP

(57) ABSTRACT

Long-acting agonistic analogs for CLR/RAMP receptors are provided that have an extended half-live in vivo.

4 Claims, 10 Drawing Sheets

(56) References Cited

OTHER PUBLICATIONS

Wu; et al., "Human vasoactive hormone adrenomedullin and its binding protein rescue experimental animals from shock", Peptides (Jul. 2008), 29(7):1223-1230.

Yang; et al., "Effects of intermedin1-53 on cardiac function and ischemia/reperfusion injury in isolated rat hearts", Biochemical and Biophysical Research Communications (Feb. 2005), 327(3):713-719.

Knudsen et al., "Potent Derivatives of Glucagon-like Peptide-1 with Pha1-macokinctic Properties Suitable for Once Daily Administration", J. Med. Chem., 2000, pp. 1664-1669, vol. 43, No. 9, American Chemical Society, Washington, D.C.

\* cited by examiner

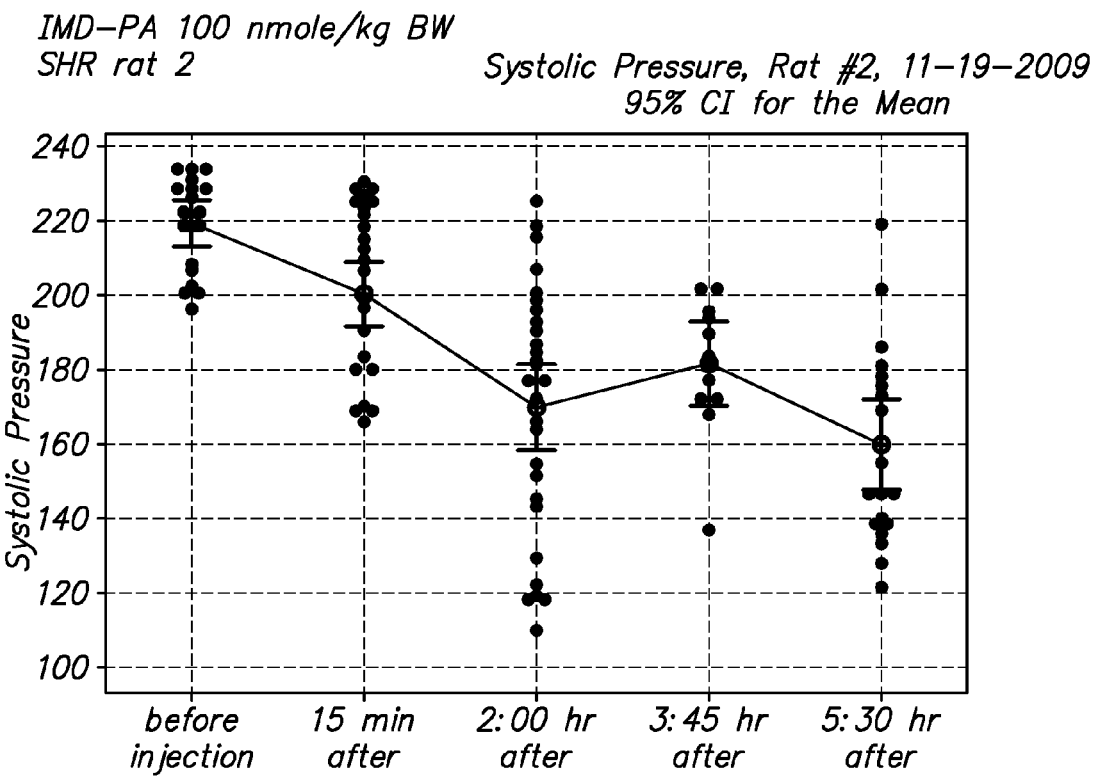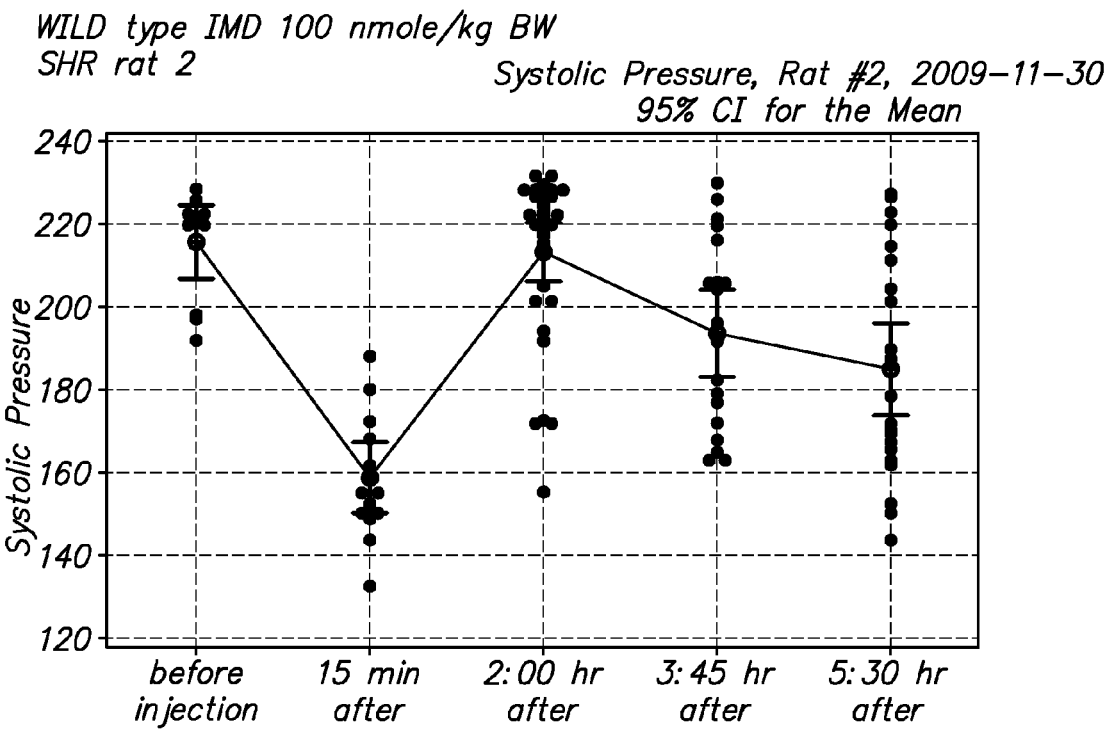

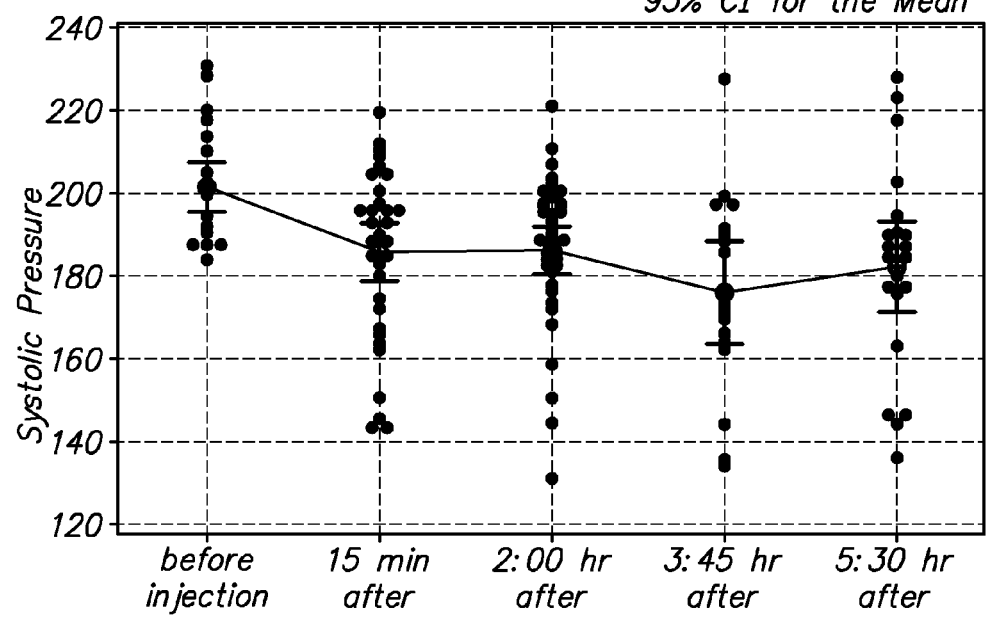

Wide type ADM

PA-conjugated ADM

US 9,694,051 B2

LONG-ACTING PEPTIDE ANALOGS

FEDERALLY SPONSORED RESEARCH AND DEVELOPMENT

This invention was made with Government support under contract DK070652 awarded by the National Institutes of Health. The Government has certain rights in the invention.

INTRODUCTION

Many aspects of physiology, including hunger, stress responses, and reproduction, are dependent on hormone balance for control. This balance can be responsive to both internal and external stimuli. For example, secretion of hormones by the anterior pituitary gland is controlled largely by the hypothalamus, a region of the brain that lies just above the gland. Hypothalamic neurons are known to make and release peptide factors that stimulate or inhibit the secretion of a particular hormone by the specific set of cells that produces it in the pituitary.

Diverse hypothalamic releasing peptides are important in the regulation of the secretion of different anterior pituitary hormones such as GH, ACTH, TSH, LH, and FSH. However, the regulation of prolactin release by the anterior pituitary is more complex, and involves stimulatory factors originating from both the hypothalamus and the intermediate lobe (see Laudon et al. (1990) *Endocrinology* 126:3185-3192; Ben-Jonathan and Hnasko (2001) *Endocr. Rev.* 22:724-763). Although the role of the intermediate lobe in the regulation of prolactin secretion is well documented, and the intermediate and posterior lobes are necessary for the suckling- and estradiol-induced rises in prolactin release, the identity of prolactin-releasing factors from the intermediate lobe remains to be characterized (Allen et al. (1995) *Endocrinology* 136:3093-3099).

The pituitary calcitonin receptor-like receptor (CRLR) has been associated with prolactin release (Meeran et al. 1997. J. Clin. Endocrinol. Metab. 82:95-100), although there is a lack of the overlapping calcitonin gene-related peptide (CGRP) expression pattern with binding sites for CGRPs in the brain (Kruger 1988. Brain Res. 463:223-244). Originally isolated as a polypeptide hormone essential for calcium balance, calcitonin belongs to a group of peptide hormones including α CGRP, β CGRP, adrenomedullin (ADM), and amylin (Eto (2001) *Peptides* 22:1693-1711). These tissue-specific peptides are important endocrine and neurocrine integrators for homeostasis maintenance in the vascular and respiratory systems.

The biological actions of these peptides are mediated via binding to two closely related type II G protein-coupled receptors (GPCRs), the calcitonin receptor and the CRLR (Christopoulos et al. (1999) *Mol. Pharmacol.* 56:235-242; Poyner et al. (2002) *Pharmacol. Rev.* 54:233-246). Although the calcitonin receptor is the main mediator for calcitonin action, it also binds amylin. Recent cloning and functional studies have shown that CGRPs, ADM, and to a lesser extent, amylin, interact with different combinations of CRLR and three receptor activity modifying proteins (RAMPs); see McLatchie et al. (1998) *Nature* 393:333-339.

Many cells express multiple RAMPs. Co-expression of the calcitonin receptor-like receptor (CRLR) and receptor activity-modifying proteins (RAMPs) is required to generate functional receptors for calcitonin gene-related peptide (CGRP) and adrenomedullin (ADM). The formation of heterodimers between RAMPs and CRLR is essential for the proper cell surface targeting and pharmacological characteristics of both CGRP and ADM receptors. The RAMP family comprises three members (RAMP1, -2, and -3), which share less than 30% sequence identity but a common topological organization. They are small intrinsic membrane proteins (predicted sizes: $M_r$ 14,000-17,000) with a large extracellular N terminus (~100 amino acids), a single trans-membrane domain, and a very short intracellular domain (10 amino acids). Co-expression of RAMP1 with CRLR leads to the formation of a CGRP receptor, whereas RAMP2 and RAMP3 promote the expression of an ADM receptor. When the calcitonin receptor is co-expressed with RAMP1 it provides for a CGRP/amylin receptor, and with RAMP3 it provides for an amylin receptor.

Studies using mutant mice deficient for α CGRP, ADM, or amylin have indicated that, in different systems, CRLR can important for cardiovascular morphogenesis, sensory neurotransmission, inflammatory reactions, nociceptive behavior, and glucose homeostasis. Thus, the physiological functions of peptides in this family are determined by receptor-binding specificity and the tissue expression profiles of individual ligands.

Peptide hormones are of great interest for clinical use and the development of therapies, including treatment of hypertension and maintenance of cardiovascular homeostasis. In addition to these effects, identification of prolcatin releasing factor is of interest. Although prolactin is important in pregnancy and lactation in mammals, and is involved in the development of the mammary glands and the promotion of milk synthesis, a specific prolactin-releasing hormone has hitherto remained unknown.

Related Publications

Hay and Smith (2001) *Trends Pharmacol. Sci.* 22:57-59; and Shindo et al. (2001) *Circulation* 104:1964-197 discuss the importance of adrenomedullin in the vasculature. The role of a CGRP is discussed by Zhang et al. (2001) *Pain* 89:265-273; Salmon et al. (1999) *Neuroreport* 10:849-854; and Salmon et al. (2001) *Nat. Neurosci.* 4:357-358. The role of amylin is discussed by Mulder et al. (2000) *Am. J. Physiol. Endocrinol. Metab.* 278:E684-691.

GenBank entry AF529213.

SUMMARY OF THE INVENTION

Long-acting peptide analogs are provided herein, which provide for the biological activities of intermedin, or of adrenomedullin, including acting as ligand for the calcitonin receptor-like receptor, but which provide for a substantially longer in vivo half-life when compared to the native polypeptide. Analogs of the invention provide for an in vivo effectiveness that lasts at least 2-fold longer in duration than the native peptide, and may be 5-fold longer, 10-fold longer, 20-fold longer, or more. The increased in vivo activity may be measured in vivo or in vitro, by determining the stability of the polypeptide, the length of the physiological effect, and the like.

In some embodiments of the invention, the analogs comprise a biologically active intermedin or adrenomedullin polypeptide that has been modified at the N-terminus. N-terminal modifications of interest include conjugation to a fatty acid, usually a C4 to C30 fatty acid, which may be unsaturated or saturated. Fatty acids of interest include, without limitation, palmitic acid; stearic acid; arachidic acid; lauric acid; myristic acid; myristoleic acid; palmitoleic acid; sapienic acid; oleic acid; linoleic acid; α-linolenic acid; arachidonic acid; eicosapentaenoic acid; erucic acid; docosahexaenoic acid; etc. In other embodiments the polypeptide is modified by pegylation, glycosylation, conjugation to large proteins such as albumin, or conjugation with polymers in combination with amino acid modifications such as the use of D-amino acid or beta amino acids to increase the biological half-life.

The analogs of the invention provide a long-acting agonistic analogs for CLR/RAMP receptors. The analogs may provide limited effect on heart rate while effecting blood pressure significantly. The compartmentalization of the long-acting peptide in serum effectively decreased the available fraction of agonists for cell stimulation at a give time point, thereby alleviating the peak and trough effects of injected peptides and eliminating unwanted side effects.

BRIEF DESCRIPTION OF THE DRAWINGS

FIGS. 1A-1C are examples of blood pressure measurements in SHR rats after treatment with a long-acting intermedin peptide (Palmitic acid-modified IMD, IMD-PA), A. 30 nmoles/kg BW; B/C, 100 nmoles/kg BW.

FIGS. 2A-2B are examples of blood pressure measurements in SHR rates after injection with a wild type intermedin peptide (IMD, 100 nmoles/kg BW). The hypotensive effects of the IMD-PA peptide lasted over five hours in vivo, whereas that of the unmodified IMD peptide lasted less than 1 hr.

FIGS. 3A-3B are BP measurements after injection with PBS in control animals.

DESCRIPTION OF THE SPECIFIC EMBODIMENTS

Figure 1A:
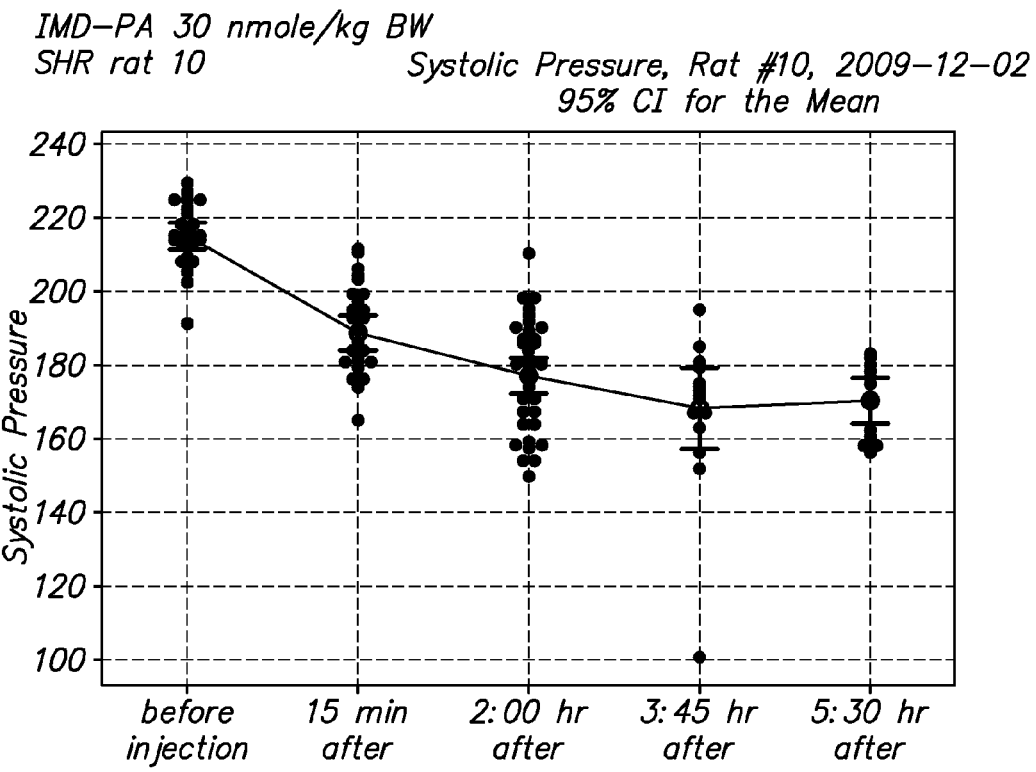

The invention provides novel polypeptide analogs of intermedin or adrenomedullin, which are members of the calcitonin peptide hormone family.

Intermedin is a ligand for the calcitonin receptor-like receptor. The human intermedin gene encodes a 148-amino-acid open reading frame, with a 24-amino-acid signal peptide for secretion at the N-terminus and a mature amidated peptide (shown in SEQ ID NO:1 and SEQ ID NO:2). Mature human intermedin peptides include without limitation a 40 amino-acid peptide (intermedin-short or IMDS), set forth as SEQ ID NO:3, which corresponds to residues 8-47 of the mature protein; and a 47-amino-acid mature peptide (intermedin-long or IMDL), set forth as SEQ ID NO:4. The intermedin peptide may be substituted with a terminal lysine residue for ease of modification. For example, an intermedin peptide of interest is as set forth in SEQ ID NO:7: K(mod)GCVLGTCQVQNLSHRLWQLMGPAGRQD-SAPVDPSSPHSY, where the terminal lysine is modified, e.g. by attachment of a lipid or other group.

Adrenomedullin is a ligand for the calcitonin receptor-like receptor. The ADM gene encodes for a preprohormone, which is posttranslationally modified to generate 2 biologically active peptides: adrenomedullin and proadrenomedullin N-terminal 20 peptide (PAMP). Adrenomedullin consists of 52 amino acids, has 1 intramolecular disulfide bond, and shows slight homology with the calcitonin gene-related peptide. The precursor, called preproadrenomedullin, is 185 amino acids long. See Genbank reference NM_001124, herein specifically incorporated by reference. The precursor polypeptide (SEQ ID NO:5) has the amino acid sequence:

MKLVSVALMYLGSLAFLGADTARLDVASEFRKKWNKWALSRGKRELRMSSSYPTGLADV

KAGPAQTLIRPQDMKGASRSPEDSSPDAARIRVKRYRQSMNNFQGLRSFGCRFGTCTVQ

KLAHQIYQFTDKDKDNVAPRSKISPQGYGRRRRRSLPEAGPGRTLVSSKPQAHGAPAPP

SGSAPHFL.

For the purposes of the invention, the term "adrenomedullin peptide" may refer to any active peptide derived from the adrenomedullin precursor peptide, unless otherwise specified. Of particular interest are hypotensive peptides. The active peptide includes, without limitation, the adrenomedullin peptide having the amino acid sequence (SEQ ID NO:6) K(mod)GCRFGTCTVQKLAHQIYQFTDKDKDNVAPR-SKISPQGY, where the lysine at residue 1 is modified, e.g. by attachment of a lipid or other group.

In some embodiments of the invention, one or more of intermedin and adrenomedullin are modified by the methods of the invention to provide for a long-lived analog.

In some embodiments of the invention, the analogs comprise a biologically active polypeptide that has been modified at the N-terminus, a shown in structure I. In other embodiments the polypeptide may be modified by pegylation, glycosylation, conjugation to large proteins such as albumin, or conjugation with polymers in combination with amino acid modifications such as the use of D-amino acid or beta amino acids to increase the biological half-life.

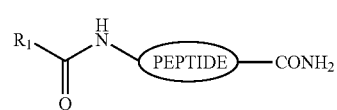

I where $R_1$ is a linear or branched $C_3$-$C_{100}$ alkyl; preferably a $C_4$-$C_{30}$ alkyl optionally substituted with halo, hydroxy, alkoxy, amino, alkylamino, dialkylamino, sulfate, or phosphate, and which may by saturated, or mono- or di-unsaturated, e.g. 18:0, 24:0 and 24:1. Fatty acids of interest include, without limitation, palmitic acid; stearic acid; arachidic acid; lauric acid; myristic acid; myristoleic acid; palmitoleic acid; sapienic acid; oleic acid; linoleic acid; α-linolenic acid; arachidonic acid; eicosapentaenoic acid; erucic acid; docosahexaenoic acid; etc.

Analogs of the invention provide for an in vivo effectiveness that lasts at least 2-fold longer in duration than the native peptide, and may be 5-fold longer, 10-fold longer, 20-fold longer, or more. The increased in vivo activity may be measured in vivo or in vitro, by determining the stability of the polypeptide, the length of the physiological effect, and the like. Of particular interest is the hypotensive effect, where a single dose of the analog peptide effective in reducing systolic blood pressure by at least about 10% is effective in maintaining reduced blood pressure for at least about 1 hour, at least about 2 hours, at least about 3 hours, at least about 4 hours, or more.

Intermedins and adrenomedullins are ligands of the CLR/RAMP receptors, and activate the receptor upon binding. Activation by intermedin results in the release of prolactin, regulation of growth hormone release, in the vascular system effects include lowering of blood pressure and vasodilation. Thus, intermedin signals through the CRLR to regulate peripheral vasodilatation-related processes. Activation by adrenomedullin results in the vascular system effects including lowering of blood pressure and vasodilation. Thus, adrenomedullin signals through the CRLR to regulate peripheral vasodilatation-related processes.

For modification by the subject methods, native intermedin, adrenomedullin or variants thereof may be used. Peptides of interest include fragments of at least about 12 contiguous amino acids, more usually at least about 20 contiguous amino acids, and may comprise 30, 35, 40 or more amino acids, up to the complete peptide, and may extend further to comprise other sequences present in the precursor protein. Deletions may extend from residue 1 through 10 of the peptide, and may further delete additionally amino acids at residues 10-15 or more. Smaller deletions, of from 1 to 5 amino acids, may be deleted in the N-terminus. Peptides of interest for therapeutic purposes may include all or substantially all of the provided peptide, or may comprise fragments thereof that retain the biological activity of intermedin.

The sequence of the polypeptide may be altered in various ways known in the art to generate targeted changes in sequence. The polypeptide will usually be substantially similar to the sequences provided herein, i.e. will differ by at least one amino acid, and may differ by at least two but not more than about ten amino acids. The sequence changes may be substitutions, insertions or deletions. Scanning mutations that systematically introduce alanine, or other residues, may be used to determine key amino acids. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine).

Modifications of interest that do not alter primary sequence include chemical derivatization of polypeptides, e.g., acetylation, or carboxylation. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the subject invention are polypeptides that have been modified using ordinary molecular biological techniques and synthetic chemistry so as to improve their resistance to proteolytic degradation or to optimize solubility properties or to render them more suitable as a therapeutic agent. For examples, the backbone of the peptide may be cyclized to enhance stability (see Friedler et al. (2000) *J. Biol. Chem.* 275:23783-23789). Analogs of such polypeptides include those containing residues other than naturally occurring L-amino acids, e.g. D-amino acids or non-naturally occurring synthetic amino acids.

The subject peptides may be prepared by in vitro synthesis, using conventional methods as known in the art. Various commercial synthetic apparatuses are available, for example, automated synthesizers by Applied Biosystems, Inc., Foster City, Calif., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

Uses of Intermedin/Adrenomedullin

In light of the pharmacologic activities of intermedin and adrenomedullin numerous clinical indications are evident, and include without limitation hypertension, for example pregnancy hypertension, pulmonary arterial hypertension, hypertension associated with diabetes, etc.; bronchopulmonary dysplasia, would healing; and the like For example, clinical indications for which an intermedin or adrenomedullin peptide or variants thereof may find use particularly in the treatment of hypertension. The analogs of the invention provide for a decrease in blood pressure, e.g. systolic pressure of at least about 5%, at least about 10%, at least about 15%, at least about 20% or more, without affecting heart rate.

Hypertension is a disease which, if untreated, strongly predisposes to atherosclerotic cardiovascular disease. It is estimated that as many as 1 in 4 adult Americans have hypertension. Hypertension is approximately twice as common in persons with diabetes as in those without. The prevalence of hypertension increases with age.

Hypertension should not be diagnosed on the basis of a single measurement. Initial elevated readings should be confirmed on at least two subsequent visits over one week or more with average diastolic blood pressure of 90 mmHg or greater or systolic blood pressure of 140 mmHg or greater required for diagnosis of hypertension. Special care is warranted in diagnosing hypertension in persons with diabetes because of greater variability of blood pressure and a much greater likelihood of isolated systolic hypertension. A goal blood pressure of less than 130/85 mmHg is recommended for these patients.

In addition to dietary changes, pharmacological treatment may be required to control high blood pressure. The subject peptides may be administered to reduce arterial blood pressure. In addition, a secondary effect of reducing hypertension is reduction of edema and inflammatory exudate volume.

Pharmaceutical compositions containing intermedin or adrenomedullin analogs are useful as cardioprotective agents, e.g. to ameliorate ischemic injury or myocardial infarct size consequent to myocardial ischemia. The development of new therapeutic agents capable of limiting the extent of myocardial injury, i.e., the extent of myocardial infarction, following acute myocardial ischemia is a major concern of modern cardiology. There has also been interest in the development of therapies capable of providing additional myocardial protection which could be administered in conjunction with thrombolytic therapy, or alone, since retrospective epidemiological studies have shown that mortality during the first few years following infarction appears to be related to original infarct size.

Myocardial ischemia is the result of an imbalance of myocardial oxygen supply and demand and includes exertional and vasospastic myocardial dysfunction. Exertional ischemia is generally ascribed to the presence of critical atherosclerotic stenosis involving large coronary arteries resulting in a reduction in subendocardial flow. Vasospastic ischemia is associated with a spasm of focal variety, whose onset is not associated with exertion or stress. The spasm is better defined as an abrupt increase in vascular tone.

The compounds of this invention can be normally administered orally or parenterally, in the treatment of patients in need of cardioprotective therapy. The dosage regimen is that which insures maximum therapeutic response until improvement is obtained and thereafter the minimum effective level that gives relief. Thus, in general, the dosages are those that are therapeutically effective in producing a cardioprotective effect, i.e., amelioration of ischemic injury or myocardial infarct size consequent to myocardial ischemia. It is also anticipated that the peptides would be useful as an injectable dosage form which may be administered in an emergency to a patient suffering from myocardial ischemia, etc.

The intermedin or adrenomedullin peptides and derivatives therefrom also find use in the reduction of edema, for example in rheumatoid arthritis, edema secondary to brain tumors or irradiation for cancer, edema resulting from stroke, head trauma or spinal cord injury, post-surgical edema, asthma and other respiratory diseases and cystoid macular edema of the eye.

Formulations

The compounds of this invention can be incorporated into a variety of formulations for therapeutic administration. Particularly, agents that modulate intermedin or adrenomedullin activity, or intermedin or adrenomedullin polypeptides and analogs thereof are formulated for administration to patients for the treatment of intermedin or adrenomedullin dysfunction, where the activity is undesirably high or low. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intracheal, etc., administration. The active agent may be systemic after administration or may be localized by the use of an implant that acts to retain the active dose at the site of implantation.

In pharmaceutical dosage forms, the compounds may be administered in the form of their pharmaceutically acceptable salts, or they may also be used alone or in appropriate association, as well as in combination with other pharmaceutically active compounds. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant is placed in proximity to the site of infection, so that the local concentration of active agent is increased relative to the rest of the body.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Typical dosages for systemic administration range from 0.1 µg to 100 milligrams per kg weight of subject per administration. A typical dosage may be one tablet taken from two to six times daily, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

Liposomes may be used for protein delivery in vivo and in vitro. The liposomes employed in the present invention can be prepared using any one of a variety of conventional liposome preparatory techniques. As will be readily apparent to those skilled in the art, such conventional techniques include sonication, chelate dialysis, homogenization, solvent infusion coupled with extrusion, freeze-thaw extrusion, microemulsification, as well as others. These techniques, as well as others, are discussed, for example, in U.S. Pat. No. 4,728,578, U.K. Patent Application G.B. 2193095 A, U.S. Pat. Nos. 4,728,575, 4,737,323, International Application PCT/US85/01161, Mayer et al., Biochimica et Biophysica Acta, Vol. 858, pp. 161-168 (1986), Hope et al., Biochimica et Biophysica Acta, Vol. 812, pp. 55-65 (1985), U.S. Pat. No. 4,533,254, Mahew et al., Methods In Enzymology, Vol. 149, pp. 64-77 (1987), Mahew et al., Biochimica et Biophysica Acta, Vol. 75, pp. 169-174 (1984), and Cheng et al., Investigative Radiology, Vol. 22, pp. 47-55 (1987). A solvent free system similar to that described in International Application PCT/US85/01161 may be employed in preparing the liposome constructions.

The materials that are utilized in preparing the liposomes include any of the materials or combinations thereof known to those skilled in the art as suitable in liposome construction. The lipids used may be of either natural or synthetic origin. Such materials include, but are not limited to, lipids such as cholesterol, phosphatidylcholine, phosphatidylethanolamine, phosphatidylserine, phosphatidylglycerol, phosphatidic acid, phosphatidylinositol, lysolipids, fatty acids, sphingomyelin, glycosphingolipids, glucolipids, glycolipids, sulphatides, lipids with amide, ether, and ester-linked fatty acids, polymerizable lipids, and combinations thereof. As one skilled in the art will recognize, the liposomes may be synthesized in the absence or presence of incorporated glycolipid, complex carbohydrate, protein or synthetic polymer, using conventional procedures. The surface of a liposome may also be modified with a polymer, such as, for example, with polyethylene glycol (PEG), using procedures readily apparent to those skilled in the art. Any species of lipid may be used, with the sole proviso that the lipid or combination of lipids and associated materials incorporated within the lipid matrix should form a bilayer phase under physiologically relevant conditions. As one skilled in the art will recognize, the composition of the liposomes may be altered to modulate the biodistribution and clearance properties of the resulting liposomes.

The membrane bilayers in these structures typically encapsulate an aqueous volume, and form a permeability barrier between the encapsulated volume and the exterior solution. Lipids dispersed in aqueous solution spontaneously form bilayers with the hydrocarbon tails directed inward and the polar headgroups outward to interact with water. Simple agitation of the mixture usually produces multilamellar vesicles (MLVs), structures with many bilayers in an onion-like form having diameters of 1-10 .mu.m (1000-10,000 nm). Sonication of these structures, or other methods known in the art, leads to formation of unilamellar vesicles (UVs) having an average diameter of about 30-300 nm. However, the range of 50 to 200 nm is considered to be optimal from the standpoint of, e.g., maximal circulation time in vivo. The actual equilibrium diameter is largely determined by the nature of the phospholipid used and the extent of incorporation of other lipids such as cholesterol. Standard methods for the formation of liposomes are known in the art, for example, methods for the commercial production of liposomes are described in U.S. Pat. Nos. 4,753,788, and 4,935,171.

Polymerized liposomes are self-assembled aggregates of lipid molecules, and are described in U.S. Pat. Nos. 5,512,294, 6,132,764, and U.S. Pat. Application 20020071843. The hydrophobic tail groups of polymerizable lipids are derivatized with polymerizable groups, such as diacetylene groups, which irreversibly cross-link, or polymerize, when exposed to ultraviolet light or other radical, anionic or cationic, initiating species, while maintaining the distribution of functional groups at the surface of the liposome. The resulting polymerized liposome particle is stabilized against fusion with cell membranes or other liposomes and stabilized towards enzymatic degradation. The size of the polymerized liposomes can be controlled by extrusion or other methods known to those skilled in the art. Polymerized liposomes may be comprised of polymerizable lipids, but may also comprise saturated and non-alkyne, unsaturated lipids. The polymerized liposomes can be a mixture of lipids, which provide different functional groups on the hydrophilic exposed surface. For example, some hydrophilic head groups can have functional surface groups, for example, biotin, amines, cyano, carboxylic acids, isothiocyanates, thiols, disulfides, α-halocarbonyl compounds, α,β-unsaturated carbonyl compounds and alkyl hydrazines. These groups can be used for attachment of nucleic acid sequences.

For use in the above described formulations, intermedin or adrenomedullin or derivatives therefrom may be synthesized and stored as a solid lyophilized powder which is reconstituted into a pharmaceutically acceptable liquid immediately prior to use. Such formulations are usually preferred because it is recognized by those skilled in the art that lyophilized preparations generally maintain pharmaceutical activity better over time than their liquid counterparts.

In addition, intermedin or adrenomedullin and their analogs could be applied topically on the skin as well as administered as aerosal sprays.

Alternatively, the peptides may be formulated as a liquid, e.g. comprising a buffer at a concentration of from about 1 mM to about 50 mM that functions to maintain the pH, wherein the anion of said buffer may be selected from the group consisting of acetate, phosphate, carbonate, succinate, citrate, borate, tartrate, fumarate and lactate; and an alcohol which may be selected from the group consisting of mannitol, sorbitol, ribotol, arabitol, xylitol, inositol, galactitol, methanol, ethanol and glycerol. Other additives may include amino acids such as methionine, arginine, lysine, glutamic acid, cysteine, glutathione, and the like, where amino acids are generally present in concentrations ranging from about 1 mM to about 100 mM. Various sugars are optionally included in the formulations, including, for example, glucose, sucrose, lactose, fructose, trehalose, mannose, and the like. Additive sugars are generally present in concentrations ranging from about 1% to about 10%.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Modification of intermedin. Peptides were synthesized on an Applied Biosystems automated peptide synthesizer by the Pan Facility at Stanford University using standard solid-phase Fmoc peptide chemistry (Fields G B, Noble R L. Solid phase peptide synthesis utilizing 9-fluorenylmethoxycarbonyl amino acids. Int J Pept Protein Res 35: 161-214, 1990). The modified peptides was synthesized by incorporating lysine residue that has been conjugated to an Fmoc-protected [C16]palmitate fatty acid (Lys(PAL)) during the synthesis of peptides. Purity was determined by reversed-phase HPLC and subsequently characterized using electrospray ionisation mass spectrometry.

The in vivo biological activity of modified and native intermedin in as set forth in FIGS. 1-4. The intermedin peptides were dissolved in saline solution with 10-20% DMSO at 10 micromoles/liter, Before injection, aliquots of peptides were dissolved in PBS to a injection final volume of 100 ul. Blood pressure measurements were made in conscious SHR rats (9-16 weeks of age) pre-adapted to the measurement procedure. Indirect systolic pressure was determined by a programmable non-invasive blood pressure system using the tail-cuff method (Kent Scientific Corporation). Following attachment of the pressure transducer, rats were left undisturbed for 10 min before base-line measurements that spanned a 15-20 minute interval. Following base-line measurements, rats were injected intraperitoneally with varying doses of peptides, or saline with 10% DMSO. Blood pressure and heart rate were monitored for 20-40 min at 30-s intervals. Changes in blood pressure were calculated as the average of measurements performed within a given time interval. The basal blood pressure of control animals are comparable to those treated with the intermedin peptide.

Figure 1B:
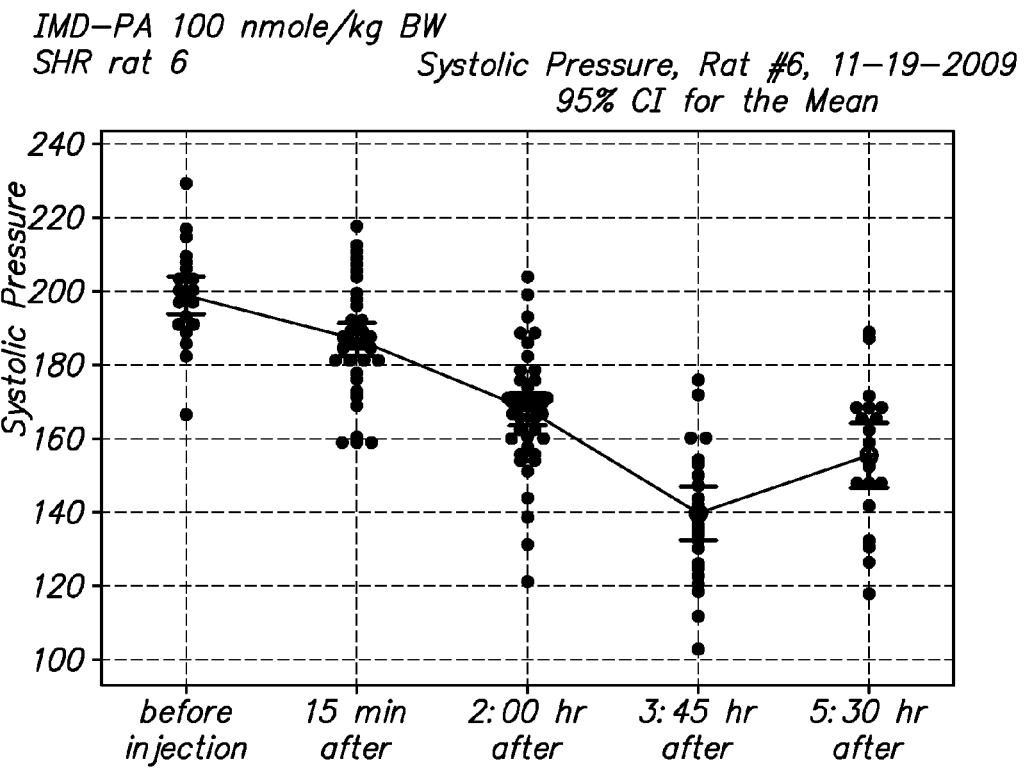
Figure 2B:
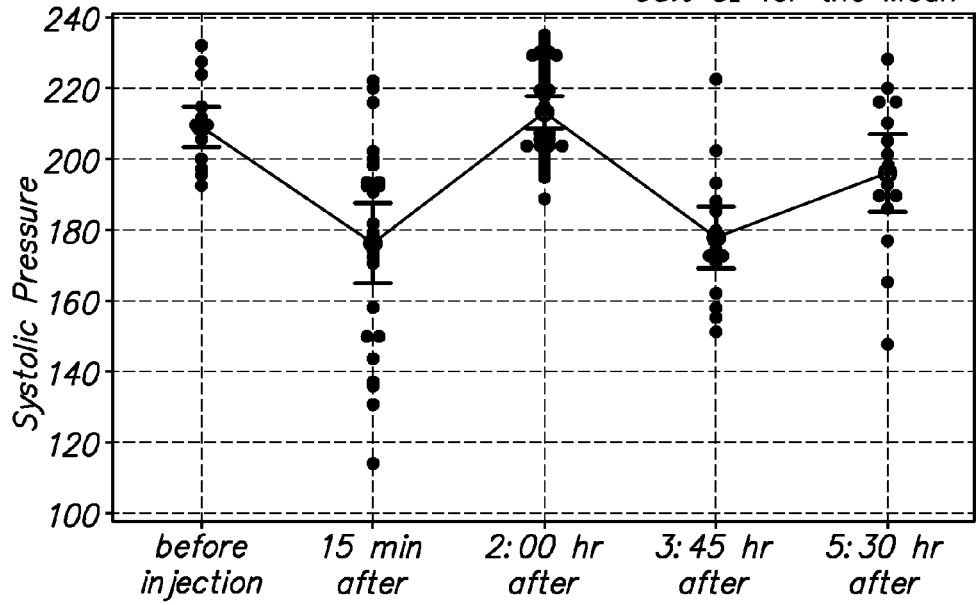
Figure 3A:
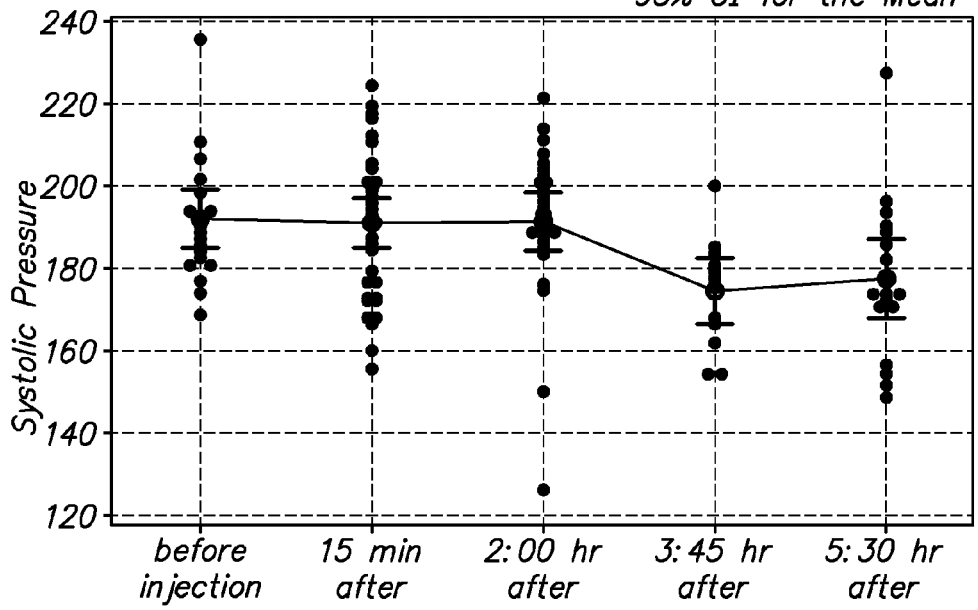
Figure 4:
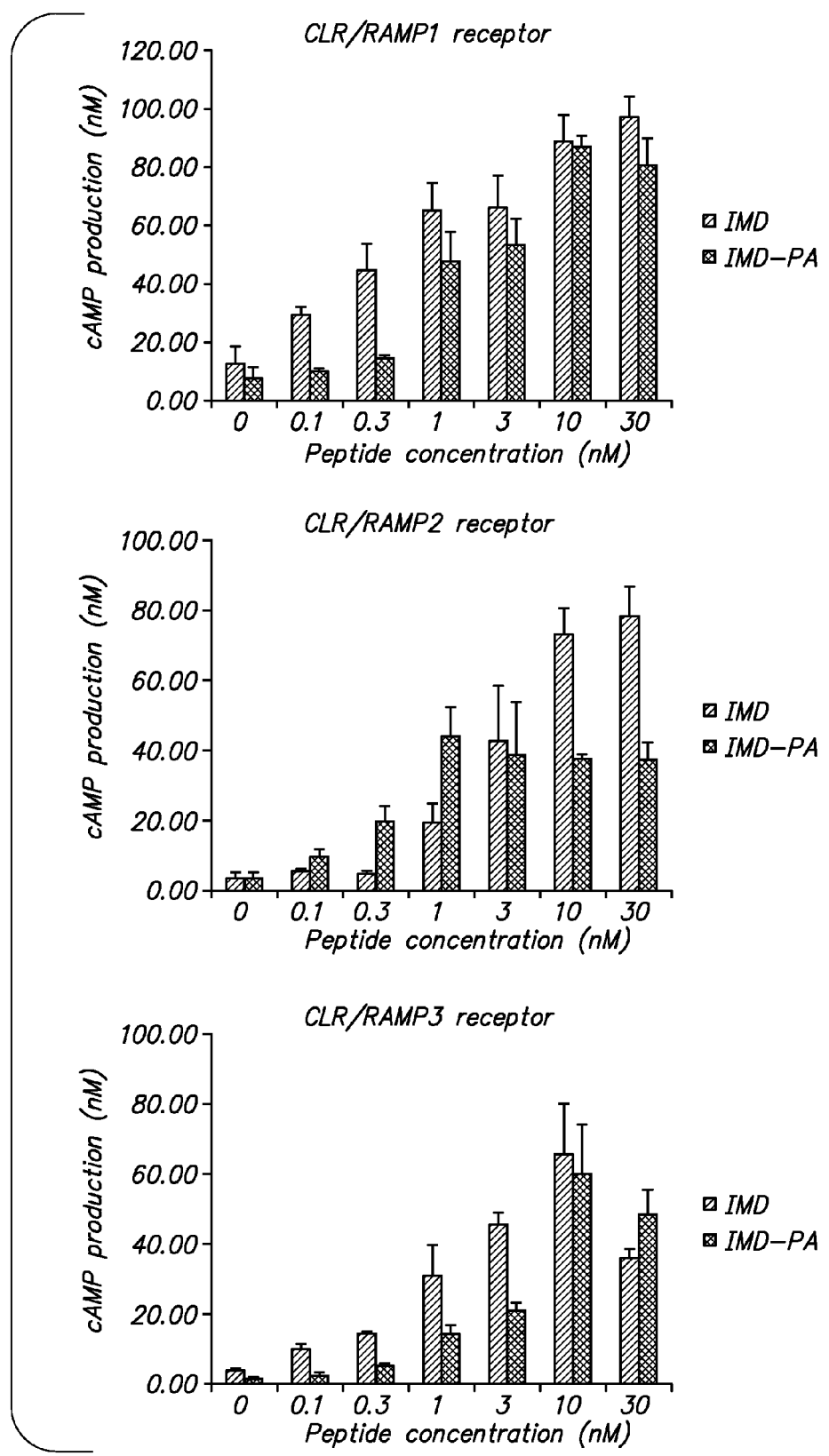
FIG. 4 shows the stimulatory effect of IMD and IMD-PA in 293T cells expressing three different receptors (CLR/RAMP1, CLR/RAMP2, and CLR/RAMP3).

As shown in FIGS. 1A-1C, when rats are injected with the modified intermedin (IMD-Palmitic acid-modified IMD) and blood pressure is measured over time, there is a significant and long lasting drop in systolic blood pressure. The hypotensive effects of this peptide lasted over five hours in vivo, whereas that of the unmodified IMD peptide lasted less than 1 hr. The results from control animals injected with PBS is depicted in FIG. 3, and from the unmodified peptide in FIG. 2.

Example 2

Modification of adrenomedullin. Peptides were synthesized on an Applied Biosystems automated peptide synthesizer by the Pan Facility at Stanford University using standard solid-phase Fmoc peptide chemistry (Fields G B, Noble R L. Solid phase peptide synthesis utilizing 9-fluorenylmethoxycarbonyl amino acids. Int J Pept Protein Res 35: 161-214, 1990). The modified peptides was synthesized by incorporating lysine residue that has been conjugated to an Fmoc-protected [C16]palmitate fatty acid (Lys(PAL)) during the synthesis of peptides. Purity was determined by reversed-phase HPLC and subsequently characterized using electrospray ionisation mass spectrometry.

Figure 7:
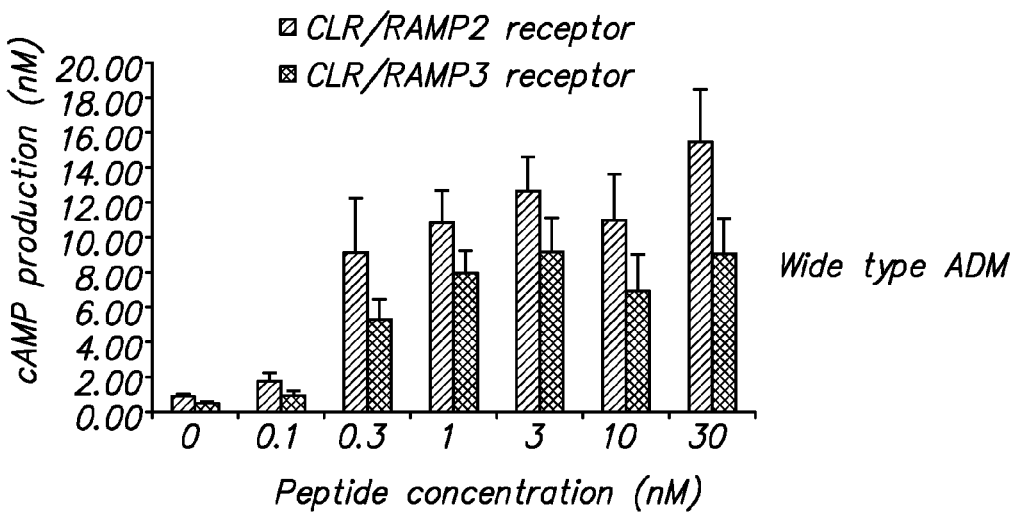
FIG. 7 shows the stimulatory effect of ADM and ADM-PA in 293T cells expressing recombinant adrenomedullin receptor 1 (CLR/RAMP2) and 2 (CLR/RAMP3). Although the stimulatory effect of ADM-PA peptide is lower than that of the wild type ADM in vitro, it has a significantly longer effective life in vivo.
Figure 7:
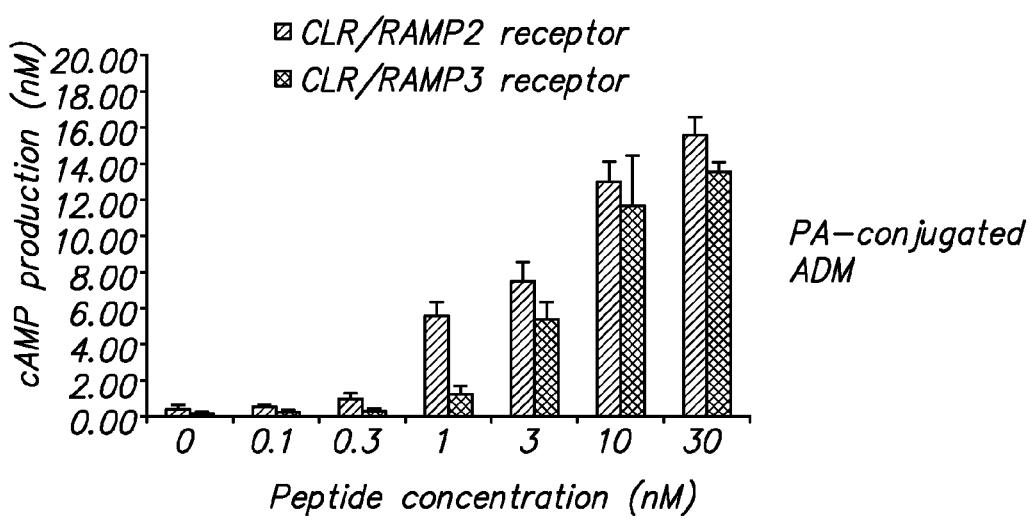

Biological activity of adrenomedullin in vitro. A typical demonstration of the stimulatory effect of ADM and ADM-PA is shown in FIG. 7.

Biological activity of adrenomedullin analog in vivo. The adrenomedullin peptides were dissolved in saline solution with 10-20% DMSO at 10 micromoles/liter, Before injection, aliquots of peptides were dissolved in PBS to a injection final volume of 200 µl. Blood pressure measurements were made in conscious SHR rats (9-16 weeks of age) pre-adapted to the measurement procedure. Indirect systolic pressure was determined by a programmable non-invasive blood pressure system using the tail-cuff method (Kent Scientific Corporation). Following attachment of the pressure transducer, rats were left undisturbed for 10 min before base-line measurements that spanned a 10-15 minute interval. Following base-line measurements, rats were injected intraperitoneally with varying doses of peptides, or saline with 10% DMSO. Blood pressure and heart rate were monitored for 20-40 min at 20-s intervals. Changes in blood pressure were calculated as the average of measurements performed within a given time interval.

The data show the systolic blood pressure profile of SHR rats after injection of the ADM-PA peptide or saline solution. (see Roh et al. Mol. Endocrinol. 2005 November; 19(11): 2824-38).

Figure 5A:
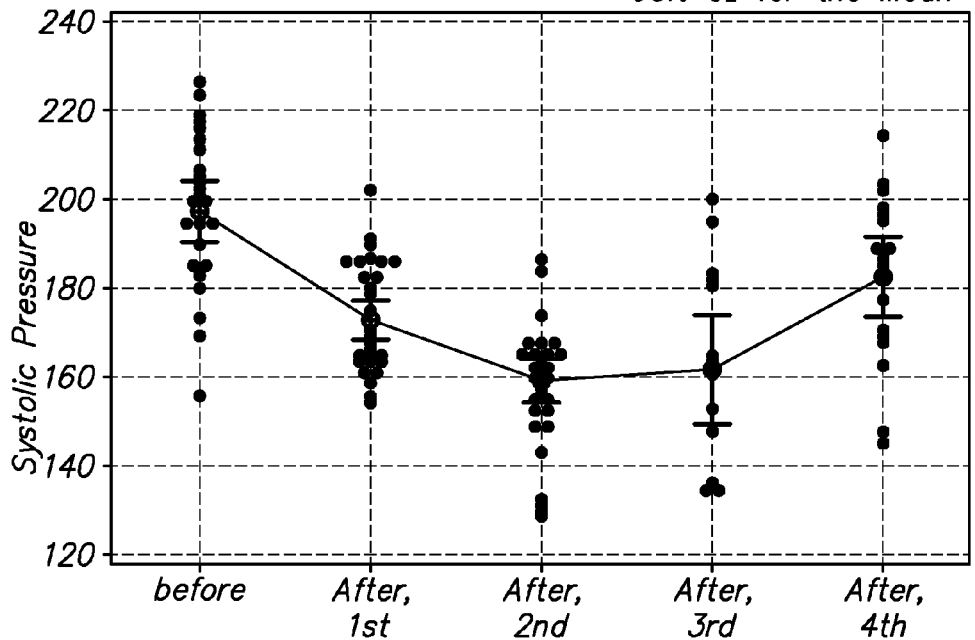
FIGS. 5A-5C show examples of systolic pressure measurement of SHR rats after an injection of a long-acting adrenomedullin peptide (Palmitic acid-conjugated ADM, ADM-PA, 100 nmoles/kg BW). The hypotensive effect of this peptide lasted over five hours in vivo. By contrast, the hypotensive effect of unmodified ADM peptide normally lasts less than 1.5 hr.
Figure 5B:
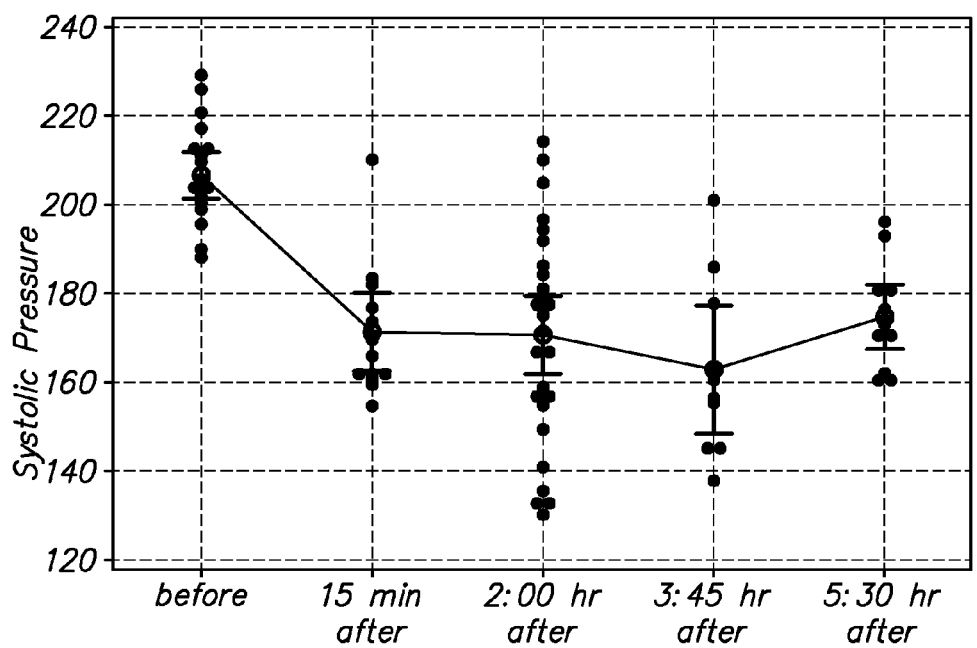
Figure 5C:
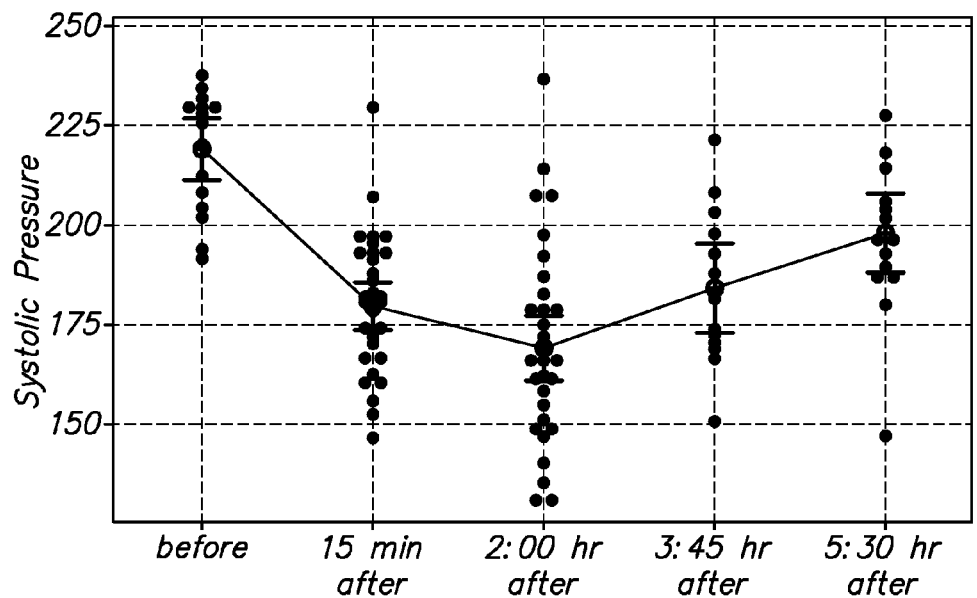
Figure 6A:
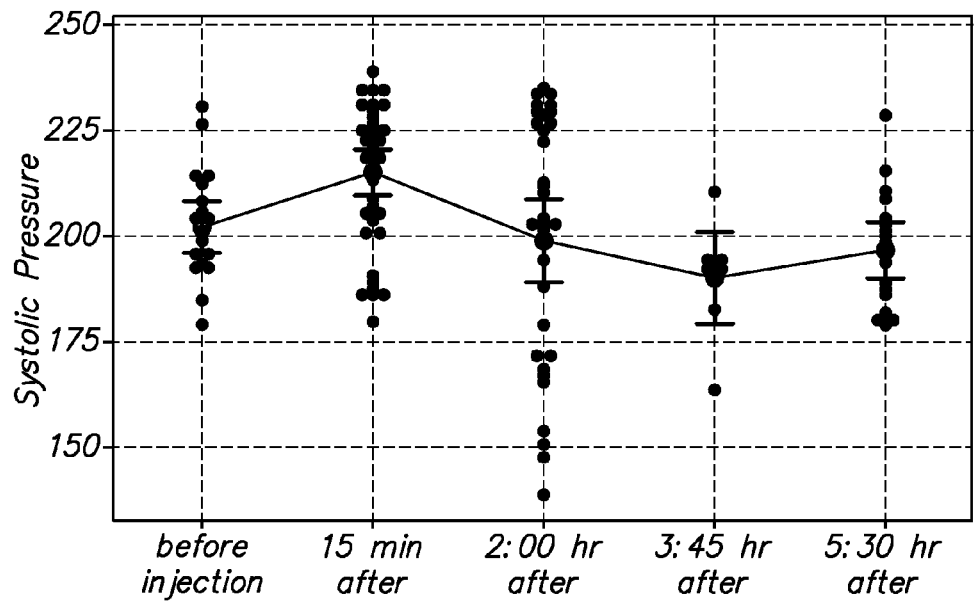
FIGS. 6A-6B show examples of systolic pressure measurement of SHR rats after an injection of control saline.
Figure 6B:
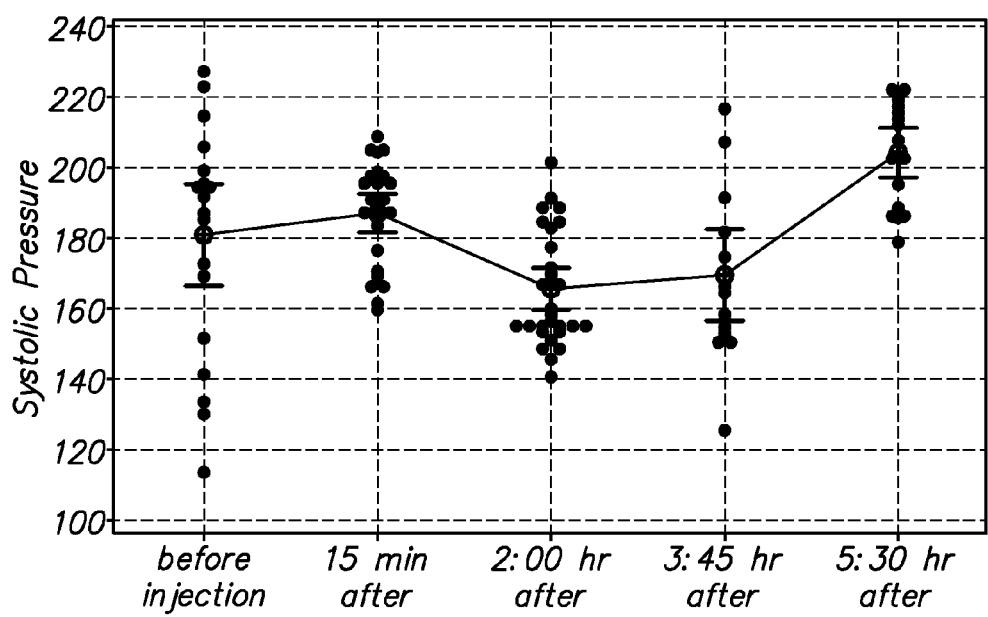
Figure 8:
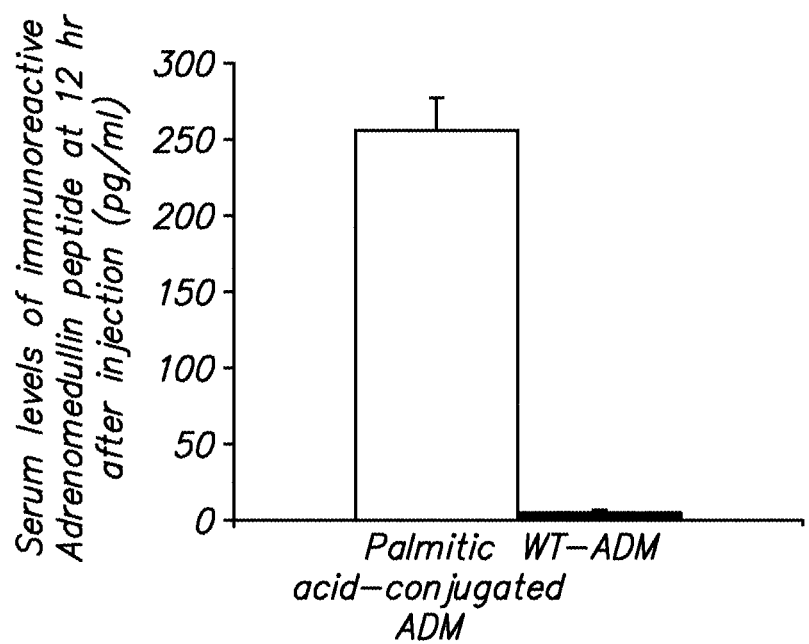
FIG. 8 shows that a significantly higher level of immunoreactive ADM-PA is retained in vivo as compared to the ADM peptide at 12 hr after i.p. injection.

As shown in FIGS. 5A-5C, when rats are injected with 100 nmoles/kg body weight of the modified adrenomedullin (ADM-Palmitic acid-modified ADM) and blood pressure is measured over time, there is a significant and long lasting drop in systolic blood pressure. The ADM-PA peptide has a long half-life as compared to ADM using based on measurement of immunoreactive ADM using ELISA (FIG. 8).

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. Moreover, due to biological functional equivalency considerations, changes can be made in protein structure without affecting the biological action in kind or amount. All such modifications are intended to be included within the scope of the appended claims.

What is claimed is:

1. A biologically active adrenomedullin peptide conjugate has the structure:

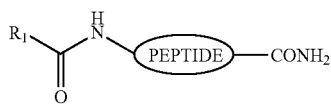

wherein said peptide consisting of SEQ ID NO: 6 and $R_1$ is a linear or branched $C_3$-$C_{100}$ alkyl optionally substituted with halo, hydroxy, alkoxy, amino, alkylamino, dialkylamino, sulfate, or phosphate, and which may by saturated, or mono- or di-unsaturated; and the conjugate having a serum half-life of greater than 1.5 hours with the alkyl moiety conjugated to the amino terminus of said SEQ ID NO: 6.

2. The peptide of claim 1, wherein $R_1$ is selected from palmitate; stearate; arachidic acid; lauric acid; myristic acid; myristoleic acid; palmitoleic acid; sapienic acid; oleic acid; linoleic acid; α-linolenic acid; arachidonic acid; eicosapentaenoic acid; erucic acid; and docosahexaenoic acid.

3. A pharmaceutical composition comprising a therapeutically effective dose of the peptide of claim 1, and a pharmaceutically acceptable excipient.

4. A biologically active human adrenomedullin peptide that consists of the amino acid sequence set forth as SEQ ID NO:6, modified by conjugation of palmitate to the amino terminus of the peptide, wherein the modified peptide has a serum half-life of greater than 1.5 hours.

* * * * *

SEQUENCE LISTING

<160> NUMBER OF SEQ ID NOS: 7

<210> SEQ ID NO 1
<211> LENGTH: 535
<212> TYPE: DNA
<213> ORGANISM: H. sapiens

<400> SEQUENCE: 1

```
cgcccacgcc cggcgccccg accgcggagg actccccgag ccccgcccgc catggcccgg      60
atcccgacgg ccgccctggg ttgcatcagc ctcctctgcc tgcagctccc tggctcgctg     120
tcccgcagcc tgggcgggga cccgcgaccc gtcaaaccca gggagccccc agcccggagc     180
ccttccagca gcctgcagcc caggcacccc gcaccccgac ctgtggtctg gaagcttcac     240
cgggccctcc aggcacagag gggtgccggc ctggcccctg ttatgggtca gcctctccgg     300
gatggtggcc gccaacactc gggcccccga agacactcgg gccccgcag acccaagcc      360 cagctcctgc gagtgggctg tgtgctgggc acctgccagg tgcagaatct cagccaccgc     420
ctgtggcaac tcatgggacc ggccggccgg caggactcag ctcctgtgga ccccagcagc     480
ccccacagct atggctgagg tggggccggg ccacacccct gccatccca gccag          535
```

<210> SEQ ID NO 2
<211> LENGTH: 148
<212> TYPE: PRT
<213> ORGANISM: H. sapiens

<400> SEQUENCE: 2

```
Met Ala Arg Ile Pro Thr Ala Ala Leu Gly Cys Ile Ser Leu Leu Cys
 1               5                  10                  15

Leu Gln Leu Pro Gly Ser Leu Ser Arg Ser Leu Gly Gly Asp Pro Arg
            20                  25                  30

Pro Val Lys Pro Arg Glu Pro Pro Ala Arg Ser Pro Ser Ser Ser Leu
        35                  40                  45

Gln Pro Arg His Pro Ala Pro Arg Pro Val Val Trp Lys Leu His Arg
    50                  55                  60

Ala Leu Gln Ala Gln Arg Gly Ala Gly Leu Ala Pro Val Met Gly Gln
65                  70                  75                  80

Pro Leu Arg Asp Gly Gly Arg Gln His Ser Gly Pro Arg Arg His Ser
                85                  90                  95

Gly Pro Arg Arg Thr Gln Ala Gln Leu Leu Arg Val Gly Cys Val Leu
            100                 105                 110

Gly Thr Cys Gln Val Gln Asn Leu Ser His Arg Leu Trp Gln Leu Met
        115                 120                 125

Gly Pro Ala Gly Arg Gln Asp Ser Ala Pro Val Asp Pro Ser Ser Pro
    130                 135                 140

His Ser Tyr Gly
145
```

<210> SEQ ID NO 3
<211> LENGTH: 40
<212> TYPE: PRT
<213> ORGANISM: H. sapiens

```
<400> SEQUENCE: 3

Val Gly Cys Val Leu Gly Thr Cys Gln Val Gln Asn Leu Ser His Arg
1               5                   10                  15

Leu Trp Gln Leu Met Gly Pro Ala Gly Arg Gln Asp Ser Ala Pro Val
            20                  25                  30

Asp Pro Ser Ser Pro His Ser Tyr
            35                  40

<210> SEQ ID NO 4
<211> LENGTH: 47
<212> TYPE: PRT
<213> ORGANISM: H. sapiens

<400> SEQUENCE: 4

Thr Gln Ala Gln Leu Leu Arg Val Gly Cys Val Leu Gly Thr Cys Gln
1               5                   10                  15

Val Gln Asn Leu Ser His Arg Leu Trp Gln Leu Met Gly Pro Ala Gly
            20                  25                  30

Arg Gln Asp Ser Ala Pro Val Asp Pro Ser Ser Pro His Ser Tyr
            35                  40                  45

<210> SEQ ID NO 5
<211> LENGTH: 185
<212> TYPE: PRT
<213> ORGANISM: H. sapiens

<400> SEQUENCE: 5

Met Lys Leu Val Ser Val Ala Leu Met Tyr Leu Gly Ser Leu Ala Phe
1               5                   10                  15

Leu Gly Ala Asp Thr Ala Arg Leu Asp Val Ala Ser Glu Phe Arg Lys
            20                  25                  30

Lys Trp Asn Lys Trp Ala Leu Ser Arg Gly Lys Arg Glu Leu Arg Met
            35                  40                  45

Ser Ser Ser Tyr Pro Thr Gly Leu Ala Asp Val Lys Ala Gly Pro Ala
            50                  55                  60

Gln Thr Leu Ile Arg Pro Gln Asp Met Lys Gly Ala Ser Arg Ser Pro
65                  70                  75                  80

Glu Asp Ser Ser Pro Asp Ala Ala Arg Ile Arg Val Lys Arg Tyr Arg
                85                  90                  95

Gln Ser Met Asn Asn Phe Gln Gly Leu Arg Ser Phe Gly Cys Arg Phe
            100                 105                 110

Gly Thr Cys Thr Val Gln Lys Leu Ala His Gln Ile Tyr Gln Phe Thr
            115                 120                 125

Asp Lys Asp Lys Asp Asn Val Ala Pro Arg Ser Lys Ile Ser Pro Gln
            130                 135                 140

Gly Tyr Gly Arg Arg Arg Arg Ser Leu Pro Glu Ala Gly Pro Gly
145                 150                 155                 160

Arg Thr Leu Val Ser Ser Lys Pro Gln Ala His Gly Ala Pro Ala Pro
                165                 170                 175

Pro Ser Gly Ser Ala Pro His Phe Leu
            180                 185

<210> SEQ ID NO 6
<211> LENGTH: 39
<212> TYPE: PRT
<213> ORGANISM: H. sapiens
<220> FEATURE:
```

```
<221> NAME/KEY: MOD_RES
<222> LOCATION: (1)...(1)
<223> OTHER INFORMATION: N terminal lysine modification with a lipid

<400> SEQUENCE: 6

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Arg Ser
            20                  25                  30

Lys Ile Ser Pro Gln Gly Tyr
        35

<210> SEQ ID NO 7
<211> LENGTH: 40
<212> TYPE: PRT
<213> ORGANISM: H. sapiens
<220> FEATURE:
<221> NAME/KEY: MOD_RES
<222> LOCATION: (1)...(1)
<223> OTHER INFORMATION: N terminal lysine modification with a lipid

<400> SEQUENCE: 7

Lys Gly Cys Val Leu Gly Thr Cys Gln Val Gln Asn Leu Ser His Arg
1               5                   10                  15

Leu Trp Gln Leu Met Gly Pro Ala Gly Arg Gln Asp Ser Ala Pro Val
            20                  25                  30

Asp Pro Ser Ser Pro His Ser Tyr
        35                  40
```